United States Patent
Taddei et al.

(10) Patent No.: US 9,718,795 B2
(45) Date of Patent: Aug. 1, 2017

(54) 1,4-CYCLOHEXYLAMINE DERIVATIVES AND PROCESSES FOR THE PREPARATION THEREOF

(71) Applicant: CHEMO RESEARCH, S.L., Madrid (ES)

(72) Inventors: Maurizio Taddei, Monteriggioni (IT); Elena Cini, Gambassi Terme (IT); Marcello Rasparini, Ghemme (IT)

(73) Assignee: CHEMO RESEARCH, S.L., Madrid (ES)

( * ) Notice: Subject to any disclaimer, the term of this patent is extended or adjusted under 35 U.S.C. 154(b) by 0 days.

(21) Appl. No.: 15/029,218

(22) PCT Filed: Oct. 14, 2014

(86) PCT No.: PCT/IB2014/065293
§ 371 (c)(1),
(2) Date: Apr. 13, 2016

(87) PCT Pub. No.: WO2015/056164
PCT Pub. Date: Apr. 23, 2015

(65) Prior Publication Data
US 2016/0257661 A1    Sep. 8, 2016

(30) Foreign Application Priority Data

Oct. 14, 2013 (IT) .................. MI2013A1693

(51) Int. Cl.
| | | |
|---|---|---|
| *C07D 295/135* | (2006.01) | |
| *C07C 275/26* | (2006.01) | |
| *C07D 233/61* | (2006.01) | |
| *C07D 295/033* | (2006.01) | |
| *C07D 295/04* | (2006.01) | |

(52) U.S. Cl.
CPC ........ *C07D 295/135* (2013.01); *C07C 275/26* (2013.01); *C07D 233/61* (2013.01); *C07D 295/033* (2013.01); *C07D 295/04* (2013.01); *C07C 2101/14* (2013.01)

(58) Field of Classification Search
None
See application file for complete search history.

(56) References Cited

FOREIGN PATENT DOCUMENTS

| WO | 2005/012266 A1 | 2/2005 |
|---|---|---|
| WO | 2010/070369 A1 | 6/2010 |

OTHER PUBLICATIONS

Agai-Csongor et al., "Discovery of Cariprazine (RGH-188): A Novel Antipsychotic Acting on Dopamine D3/D2 Receptors," Bioorganic & Medicinal Chemistry Letters 22(10):3437-3440 (2012).
Agai-Csongor et al., "Novel Sulfonamides Having Dual Dopamine D2 and D3 Receptor Affinity Show in Vivo Antipsychotic Efficacy with Beneficial Cognitive and EPS Profile," Bioorganic & Medicinal Chemistry Letters 17(19):5340-5344 (2007).
International Search Report and Written Opinion corresponding to PCT/IB2014/065293, filed Oct. 14, 2014 (mailed Jan. 26, 2015).

*Primary Examiner* — Golam M M Shameem
*Assistant Examiner* — Laura Daniel
(74) *Attorney, Agent, or Firm* — LeClairRyan, a Professional Corporation

(57) ABSTRACT

The invention relates to a process for the synthesis of Cariprazine, an antipsychotic compound useful in the treatment of positive and negative symptoms associated to schizophrenia, with the following structural formula: (A) The invention further relates to the synthesis of intermediates useful in the preparation of Cariprazine.

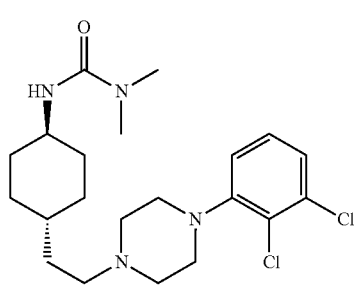

(A)

9 Claims, No Drawings

1,4-CYCLOHEXYLAMINE DERIVATIVES AND PROCESSES FOR THE PREPARATION THEREOF

This application is a national stage application under 35 U.S.C. §371 of PCT Application No. PCT/IB2014/065293, filed Oct. 14, 2014, which claims the priority benefit of Italy Application No. MI2013A001693, filed Oct. 14, 2013, the disclosures of which are incorporated herein by reference in their entirety.

FIELD OF THE INVENTION

The present invention relates to an industrially viable and advantageous process for the preparation of Cariprazine or of intermediates useful in the synthesis thereof.

STATE OF THE ART

N-[trans-4-[2-[4-(2,3-dichlorophenyl)piperazin-1-yl]ethyl]cyclohexyl]-N',N'-1-dimethylurea, generally known as Cariprazine, is an antipsychotic useful in the treatment of positive and negative symptoms associated to schizophrenia due to its ability to act as a partial agonist of dopamine receptors $D_2/D_3$. This compound has the following chemical structure:

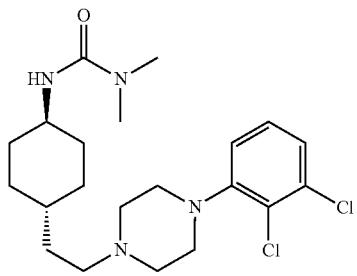 [SMILES: CN(C)C(=O)N[C@H]1CC[C@H](CCN2CCN(c3cccc(Cl)c3Cl)CC2)CC1]

Due to its activity as a partial agonist, Cariprazine inhibits dopamine receptors when these are over-stimulated (performing an antagonist function) or stimulating the same receptors when the level of endogenous dopamine is too low.

Cariprazine also acts on $5\text{-}HT_{1a}$ receptors, although its affinity towards the latter is considerably lower than that for dopamine receptors.

Cariprazine and other similar compounds were first disclosed in international patent application WO 2005/012266 A1. This application describes two alternative routes of synthesis for the preparation of Cariprazine, as schematized below:

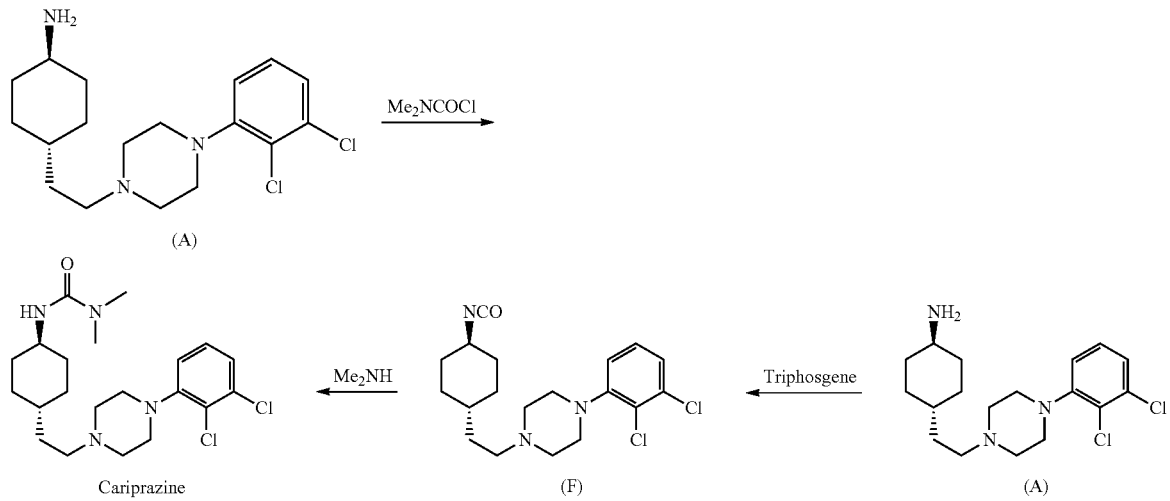

According to a first possibility, Cariprazine can be prepared starting from amine (A) by treatment with dimethylcarbamoyl chloride; alternatively, it is possible to treat amine (A) with triphosgene $(CO(OCCl_3)_2)$ to transform it into the corresponding isocyanate (F), and reacting the latter with dimethyl amine. Drawbacks associated with these processes are in the former case the high toxicity and probable cancerogenicity of dimethylcarbamoyl chloride; in the latter case, the need to use triphosgene (an extremely dangerous compound) or one of its precursor in order to prepare isocyanate (F).

The amine (A), starting compound for the procedures described in the application cited above, can be prepared according to the procedure described in international patent application WO 2003/029233 A1, schematized below, by reductive amination of N-Boc protected trans-(4-aminocyclohexyl)acetaldehyde (B) with 1-(2,3-dichlorophenyl)piperazine (C) in the presence of sodium triacetoxyborohydride to yield N-Boc protected trans-4-(2-(4-(2,3-dichlorophenyl)piperazin-1-yl)ethyl)cyclohexylamine (D), which is subsequently converted into the hydrochloride salt of amine (A) by treatment with a solution of hydrogen chloride in ethyl acetate:

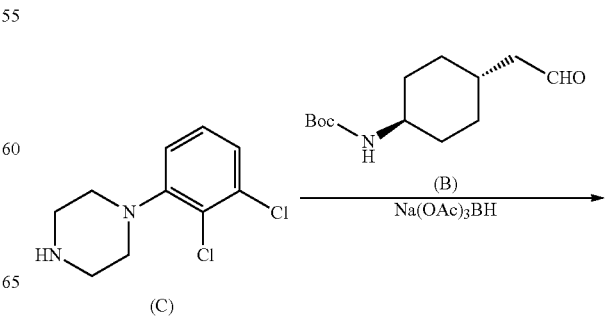

-continued

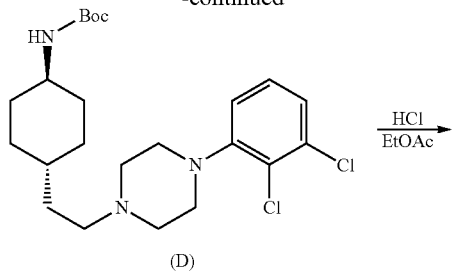

(D)

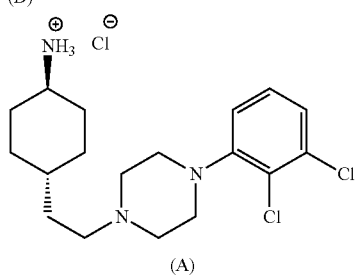

(A)

The N-Boc protected trans-(4-aminocyclohexyl)acetaldehyde (B), in its turn, can be prepared starting from 4-nitrophenylacetic acid which is reduced to 4-aminocyclohexylacetic acid and subsequent separation of cis- and trans-isomers by fractional crystallization of the hydrochloride salts of the corresponding ethyl esters, as described in international patent application WO 2010/070368 A1. Ester (E), with the desired stereochemistry, is then converted into aldehyde (B) by protecting the amino group with di-tert-butyl dicarbonate ($Boc_2O$) and selective reduction with di-iso-butylaluminium hydride (Dibal-H) at −78° C.:

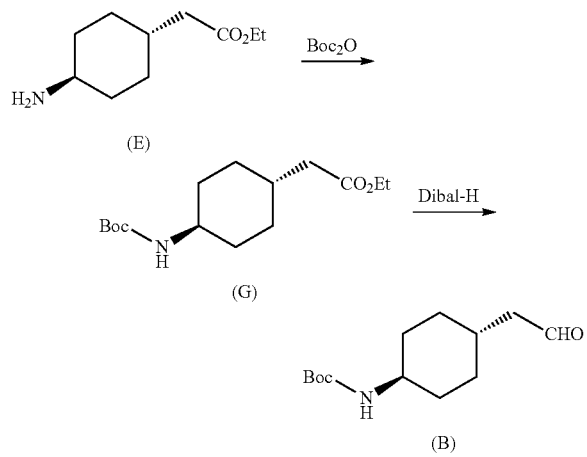

A drawback consists in the need to carry out said reaction at cryogenic temperatures to avoid the formation of significant amounts of the alcohol, product of over-reduction of the desired aldehyde. Performing a reaction at cryogenic temperatures at the industrial scale, although feasible, entails the use of appropriate equipments not always available in multipurpose plants.

An alternative procedure for the preparation of Cariprazine has been disclosed in international patent application WO 2010/070369 A1. This synthetic approach involves the reduction of ethyl ester (G) to yield the corresponding alcohol which, activated as mesylate, is reacted with 1-(2,3-dichlorophenyl)piperazine (C) to yield N-Boc protected trans-4-(2-(4-(2,3-dichlorophenyl)piperazin-1-yl)ethyl)cyclohexylamine (D):

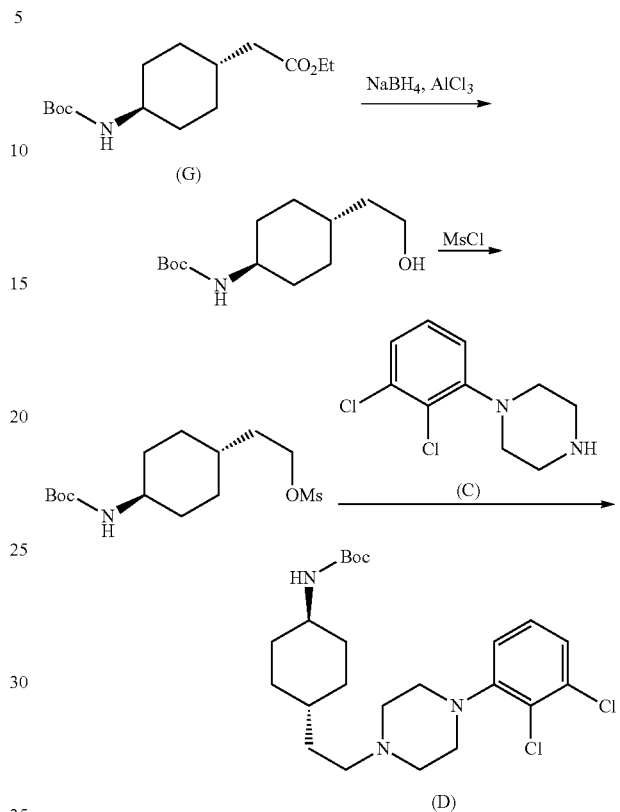

However, it is known that alkyl sulfonates (e.g. mesylates and tosylates) and alkyl halides, due to their alkylating properties, are considered genotoxic or potential genotoxic substances, as they can react with the DNA leading to mutations (*Organic Process Research & Development* (2010), 14, 1021-1026 and citations therein).

An innovative synthetic approach for the preparation of substituted amines by direct alkylation of alcohols, known as "hydrogen borrowing", has been recently described in *Chem Cat Chem* (2011), 3, 1853-1864.

This emerging technology is very attractive from the standpoint of chemical processes sustainability because it allows the substitution of highly reactive compounds, such as alkyl halides, mesylates or tosylates with less reactive compounds, such as alcohols, further to allowing a reduction in the number of synthetic steps.

Since in pharmaceutical active principles very low amounts of genotoxic or potentially genotoxic substances are generally tolerated, pharmaceutical companies are strongly interested in developing processes not entailing the use of alkylating reagents, according to the "Quality by Design" approach, that is increasingly required by regulatory agencies.

It is an object of the present invention to provide a method for preparing Cariprazine or intermediates useful in the synthesis thereof, characterized by high yields avoiding the use of dangerous reagents and providing the desired products with a purity appropriate for use in pharmaceuticals.

SUMMARY OF THE INVENTION

These objectives are achieved with the present invention which, in a first aspect thereof, relates to a process for the preparation of piperazines of general formula (II) or salts thereof:

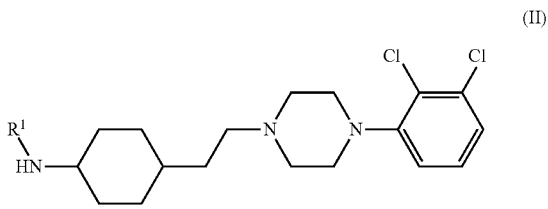

(II)

said process comprising the following synthetic steps:
a) preparing an alcohol of general formula (I)

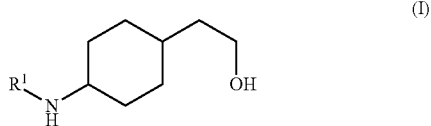

(I)

wherein $R^1$ is selected between —C(O)N(CH$_3$)$_2$ or an amine protecting group (Pg);
b) directly alkylating the 1-(2,3-dichlorophenyl)piperazine (C) with the alcohol of general formula (I):

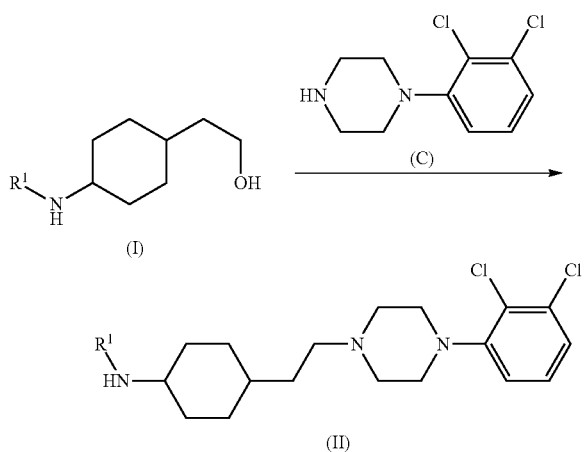

Suitable amine protecting groups (Pg) are the carbamates, for example tert-butoxycarbonyl (Boc) or benzyloxycarbonyl (Cbz).

DETAILED DESCRIPTION OF THE INVENTION

All terms used in the present application, unless otherwise indicated, must be interpreted in their ordinary meaning as known in the field. Other more specific definitions for some terms used in the present application are given below and are intended to be applied uniformly to the entire description and claims, unless otherwise indicated.

The symbol ″″″ (dashed bond) present in some of the formulas of the description and the claims indicates that the substituent is directed below the plane of the sheet.

The symbol ▬ (wedge bond) present in some of the formulas of the description and the claims indicates that the substituent is directed above the plane of the sheet. The compounds prepared by the processes of the present invention can exist, be used or be isolated in the form of 1,4-cis or 1,4-trans-isomers of the cyclohexane. It should be understood that the processes of the present invention may give rise to these isomers in purified form or mixtures thereof. The procedures for the purification and characterization of these compounds are known to the man skilled in the art and include, for example, fractional crystallization techniques or chromatography. The compounds object of the present invention preferably possess 1,4-trans relative configuration.

In general, the nomenclature used in this Application is based on AUTONOM™ v.4.0, a Beilstein Institute computerized system for the generation of IUPAC systematic nomenclature. If there is a discrepancy between a depicted structure and a name given to that structure, the depicted structure should be considered correct. Furthermore, if the stereochemistry of a structure or a portion of a structure is not indicated with, for example, wedge or dashed bonds, the structure or portion of the structure has to be interpreted as encompassing all of its stereoisomers.

It should also be understood that each compound described in the present invention can represent a salt or a co-crystal thereof.

According to its most general aspect, the present invention relates to the preparation of piperazines of general formula (II) or salts thereof.

The first step of the process of the invention, a), consists in the preparation of an alcohol of general formula (I). This step can be performed according to three alternative routes of synthesis a.i), a.ii) and a.iii).

The synthetic scheme a.i) can be carried out when $R^1$=—C(O)N(CH$_3$)$_2$ and includes the following steps:

a.i.1) treating aminoester (IV) with carbonyldiimidazole (CDI):

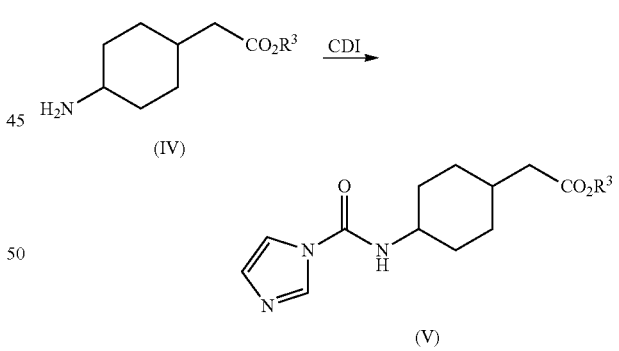

a.i.2) converting imidazolide (V) into urea (VI) by treatment with dimethylamine or a salt thereof:

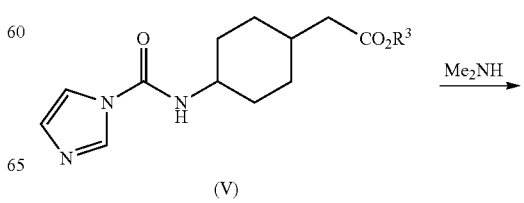

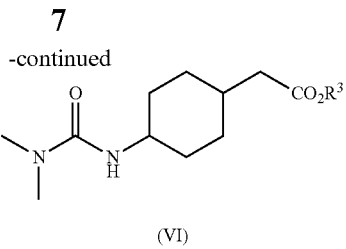

a.i.3) reducing the ester portion of urea (VI) to provide the alcohol of formula (I'):

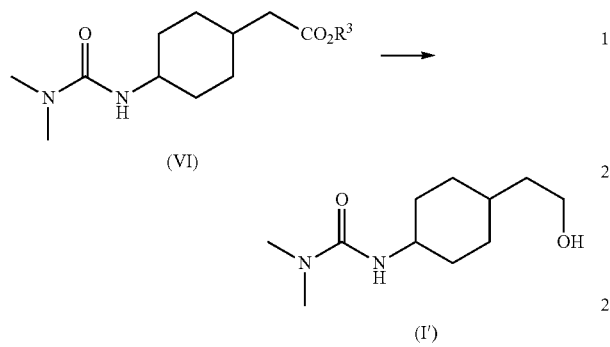

wherein $R^3$ is chosen among an optionally substituted linear or branched C1-C6 alkyl (e.g. methyl, ethyl, n-propyl, iso-propyl, n-butyl, iso-butyl, tert-butyl) or benzyl.

Step a.i.1) includes the treatment of aminoester (IV) (optionally in the form of a salt) con CDI to obtain imidazolide (V). The N-acylation reaction is normally carried out in an aprotic polar solvent, e.g. dimethylacetamide, dimethylformamide, N-methylpyrrolidone, dimethylsulfoxide, tetrahydrofuran, acetonitrile, ethyl acetate or a mixture thereof. The amount of CDI useful for the aim is between 1 and 1.5 equivalents with respect to the amount of aminoester (IV) used, preferably comprised between 1.1 and 1.3 equivalents.

The next step a.i.2) entails the transformation of imidazolide (V), optionally isolated, into urea (VI) by treatment with dimethylamine (or a salt thereof) in an aprotic polar solvent, such as for example, dimethylacetamide, dimethylformamide, N-methylpyrrolidone, ethyl acetate, tetrahydrofuran, acetonitrile, or in a chlorinated solvent, such as dichloromethane, or a mixture thereof. Dimethylamine or the salt thereof are used in a amount between 1 and 1.5 equivalents with respect to the amount of imidazolide (V) used.

When urea (VI) is used in the form of a salt thereof (e.g. its hydrochloride salt) it is required the addition of an organic base, such as a tertiary amine, e.g. triethylamine, N,N-diisopropylethylamine, N,N-diisopropylmethylamine, N-methylmorpholine or N,N-dicyclohexylmethylamine. The amount of base is between 1 and 2.5 equivalents with respect to the amount of the salt of dimethylamine used, preferably 2 equivalents.

The last step a.i.3) entails the reduction of the ester portion of urea (VI) to obtain the alcohol of general formula (I'). This step can be carried out by treatment with a reducing agent capable to selectively reduce an ester into an alcohol in the presence of an urea, for example chosen among Dibal-H, sodium borohydride ($NaBH_4$), calcium borohydride ($Ca(BH_4)_2$) or lithium borohydride ($LiBH_4$) in a amount between 1 and 5 equivalents, preferably between 2 and 3 equivalents, with respect to the amount of urea (VI) used. When this step is carried out using Dibal-H as the reducing agent, polar or apolar aprotic solvents, such as toluene, tetrahydrofuran, dichloromethane or a mixture thereof can be used; when this step is carried out with a boron-containing reducing agent, suitable solvents are ethers, such as tetrahydrofuran, optionally in mixture with an alcohol, such as methanol.

The alternative synthetic scheme a.ii) can be performed when $R^1$ is an amino protecting group (Pg) and includes the following steps:

a.ii.1) protecting the amount in of aminoester (IV):

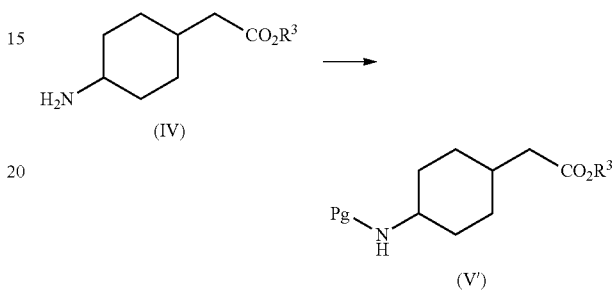

a.ii.2) reducing the ester portion of carbamate (V') to obtain alcohol (I''):

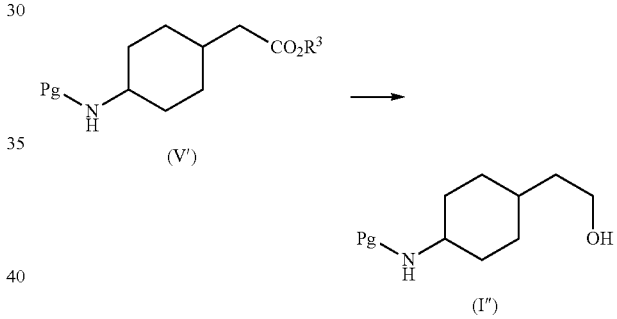

wherein $R^3$ and Pg have the meanings given above.

Step a.ii.1) includes the protection of amino group as a carbamate according to one of the procedures described in Theodora W. Green, *Protective Groups in Organic Synthesis*, John Wiley & Sons (1999), pages 503-550, which are herein incorporated by reference. Preferably this step can be performed by treatment with di-tert-butyldicarbonate ($Boc_2O$), benzyl chloroformate (CbzCl), N-(benzyloxycarbonyloxy)succinimide (Cbz-OSu) or dibenzyl dicarbonate ($Cbz_2O$) in an aprotic polar solvent, such as for example dimethylacetamide, dimethylformamide, N-methylpyrrolidone, ethyl acetate, tetrahydrofuran, acetonitrile, or in a chlorinated solvent, such as dichloromethane, or a mixture thereof, optionally in the presence of a tertiary amine.

The following step a.ii.2) entails the reduction of the ester portion of carbamate (V') to obtain alcohol (I'') using one of the methods known in the field, for example one of those described above to carry out step a.i.3).

Scheme a.iii) can be performed when $R^1$=—C(O)N $(CH_3)_2$ and includes the following steps:

a.iii.1) converting aminoester (IV) or a salt thereof into urea (VI) by treatment with a compound of general formula (VII):

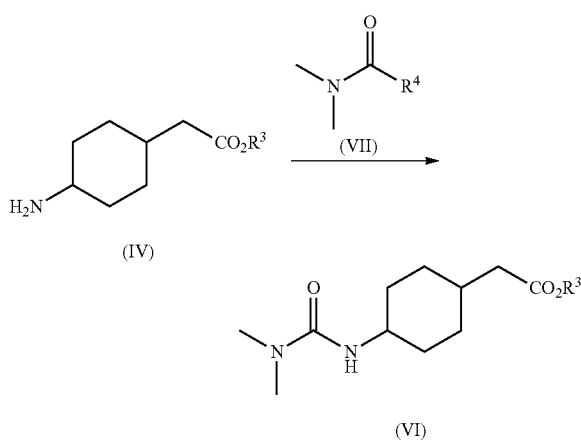

wherein R⁴ is imidazol-1-yl;

a.iii.2) reducing the ester portion of urea (VI) to yield alcohol (I').

Step a.iii.1) includes the treatment of aminoester (IV), or a salt thereof (preferably its hydrochloride salt), with a compound of general formula (VII) to yield urea (VI). The acylation reaction is normally carried out in an aprotic polar solvent, for example one of those described above to perform step a.i.1). The amount of compound of general formula (VII) may vary between 1 and 1.5 equivalents with respect to the amount of aminoester (IV) used, preferably 1.2 equivalents.

When aminoester (IV) is used in the form of a salt thereof (such as its hydrochloride) it is required the addition of an organic base such as a tertiary amine, e.g. triethylamine, N,N-diisopropylethylamine, N,N-diisopropylmethylamine, N-methylmorpholine or N,N-dicyclohexylmethylamine. The amount of base is between 1 and 5 equivalents with respect to the amount of the salt of aminoester (IV) used, preferably 3 equivalents.

The next step a.iii.2) entails the reduction of the ester portion of urea (VI) to obtain alcohol (I') using one of the procedures described above to perform step a.i.3).

The second operation of the process of the invention, b), consists in the direct alkylation of the 1-(2,3-dichlorophenyl)piperazine (C) with an alcohol of general formula (I) (in particular, with an alcohol of formula (I') or (I"), as described above). The direct alkylation of the 1-(2,3-dichlorophenyl)piperazine (C) with the alcohol (I) to yield a piperazine of general formula (II) is normally carried out in the presence of a catalyst comprising a transition metal, optionally in the presence of a ligand, in an apolar solvent (e.g. cyclohexane, xylene or preferably toluene) or in a protic or aprotic polar solvent (for example 1,4-dioxane, tetrahydrofuran, methyltetrahydrofuran, 1,2-dimethoxyethane, tert-butyl alcohol or preferably tert-amyl alcohol).

The transition metal is preferably chosen among rhodium, nickel, palladium, platinum, iridium, ruthenium or a mixture thereof and can be used in metallic form (oxidation state zero) or in the form of a salt or of a coordination complex thereof.

Said transition metal can optionally be supported on a solid matrix, such as carbon, silica or alumina or an organic polymer matrix. Alternatively it can be used in the form of nanoparticles.

Preferably the reaction is performed under homogenous catalysis conditions and the transition metal is used in the form of a coordination complex soluble in the reaction medium, optionally coordinated with a mono- or polidentate ligand, preferably a phosphine.

Useful catalysts include for example ruthenium supported on carbon, alumina or magnetite, such as $RuCl_3*(H_2O)_x$, $Ru(OH)_x/TiO_2$ o $Ru(OH)_x/Al_2O_3$, $(\eta^5-C_5Ph_4O)_2HRu_2H(CO)_4$ (Shvo catalyst), $[Ru(p-cymene)Cl_2]_2$, $[Ru_3(CO)_{12}]$, $[RuH_2(CO)(PPh_3)_3]$, $[RuH_2(PPh_3)_4]$, $[RuH(CO)(PPh_3)_4]$, $[RuC_{12}(PPh_3)_4]$, $[RuHCl(CO)(PPh_3)_3]$, $[Ru(arene)Cl_2]_2$ (wherein arene is benzene, p-cymene o mesitylene), or $[(\eta^6-p-cymene)Ru(L)(Cl)][PF_6]$ (wherein L is an N-heterocyclic carbene ligand such as for example, 3-methyl-1-(2-picolyl)imidazol-2-ylidene or 3-isopropyl-1-(2-picolyl)imidazol-2-ylidene).

Alternatively the catalyst can be iridium-based, for example $[Cp*IrCl_2]_2$, $[Ir(COD)C_1]_2$, $[Cp*Ir(NH_3)_3][I]_2$, or $IrCl_3$ wherein COD is 1,4-cyclooctadiene and Cp* is pentamethylcyclopentadienyl.

In case of homogenous catalysis, said transition metal can be coordinated with a bidentate phosphine, such as dppf, DPEPhos, Xantphos or BINAP:

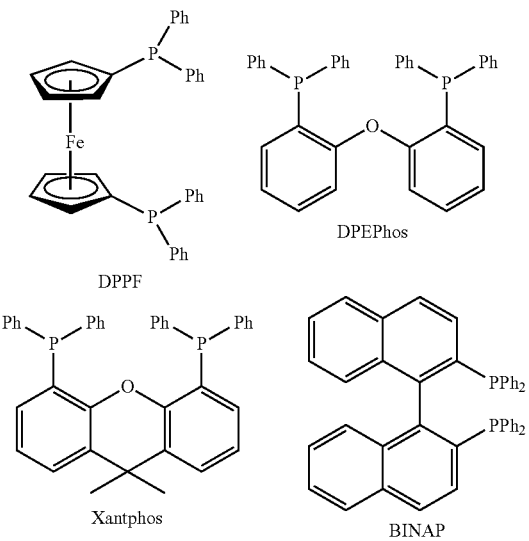

The molar amount of catalyst is comprised between 1/10000 and 1/10 with respect to the amount of alcohol of general formula (I) used.

The 1-(2,3-dichlorophenyl)piperazine (C) used as starting compound in the alkylation reaction is commercially available and can be prepared according to standard techniques in organic synthesis.

Preferably the alcohol used as reagent in the direct alkylation of 1-(2,3-dichlorophenyl)piperazine (C) in operation b) of the process, is a trans-2-(4-aminocyclohexyl)ethanol of general formula (IA):

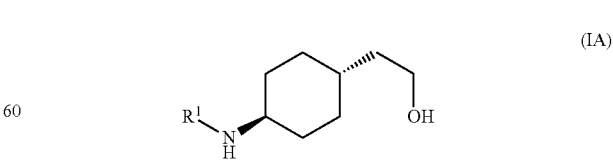

In this case, the process leads to the formation of a piperazine of general formula (IIA) in which the substituents attached to cyclohexane ring possess 1,4-trans relative configuration:

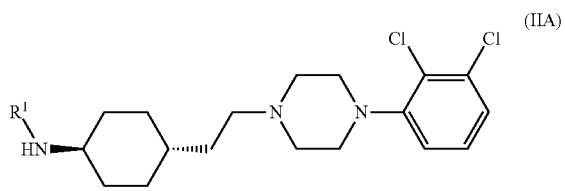

In a further preferred aspect of the invention, the compounds of general formula (II"), reported below, are converted into a partial agonist of $D_2/D_3$ receptors (II'), a salt or a co-crystal thereof:

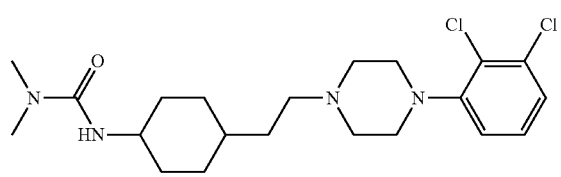

The process of this preferred aspect of the invention includes the following steps:

b') directly alkylating the 1-(2,3-dichlorophenyl)piperazine (C) with the alcohol of general formula (I"):

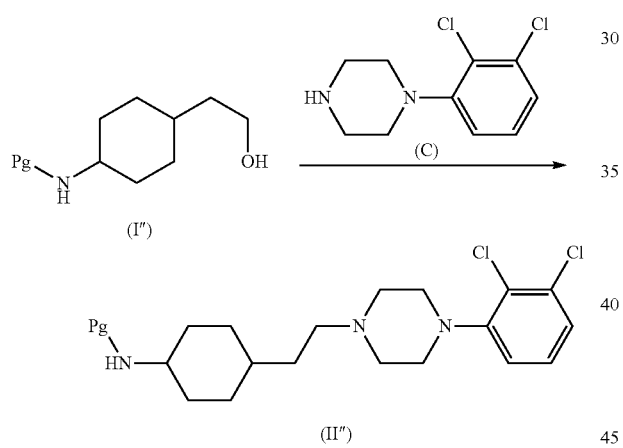

c) deprotecting the compound of general formula (II"):

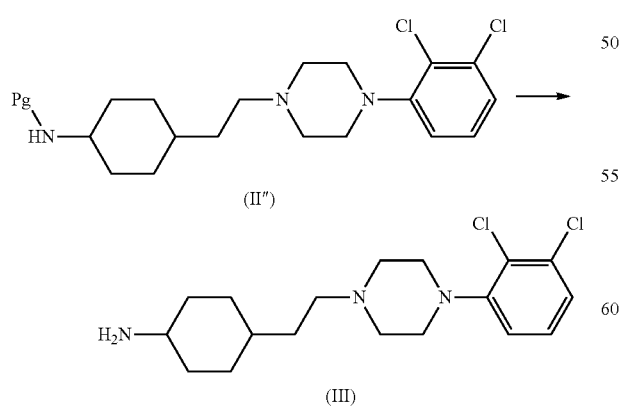

d) converting the piperazine of general formula (III) or a salt thereof into a partial agonist of $D_2/D_3$ receptors (II') by treatment with a compound of general formula

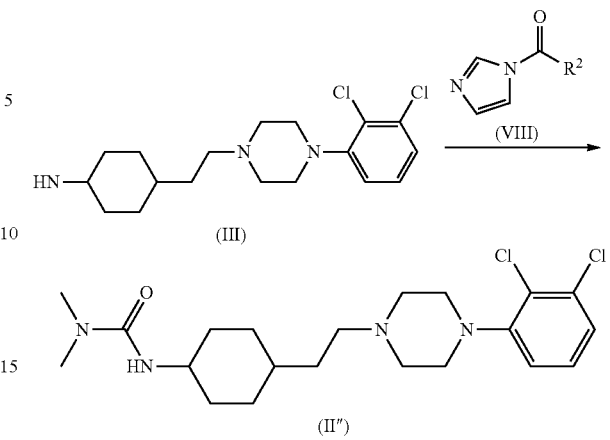

Step b') corresponds to operation b) of the process object of the most general aspect of the present invention, using, in the place of alcohol (I), the alcohol of general formula (I"):

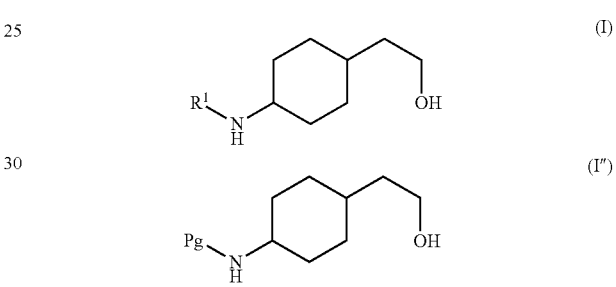

Step c) includes the deprotection of the compound of general formula (II"). This step can be performed using one of the methods known to the person skilled in the art, for example one of those described in Theodora W. Green, *Protective Groups in Organic Synthesis*, John Wiley & Sons (1999), pages 503-550, which are herein incorporated by reference. For example, this step can be carried out by treatment with phosphoric acid, trifluoroacetic acid (TFA), a solution of hydrogen chloride in water or in an organic solvent, or by treatment with formic acid.

The next step d) involves the transformation of piperazine of general formula (III) or a salt thereof into a partial agonist of $D_2/D_3$ receptors (II') by treatment with a compound of formula (VIII):

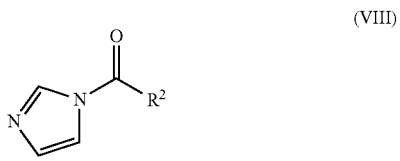

wherein $R^2$ is selected between imidazol-1-yl or $-N(CH_3)_2$.

This operation can be performed according to two alternative synthetic schemes, d.i) and d.ii).

Scheme di) can be carried out when $R^2$ is $-N(CH_3)_2$, and includes the treatment of the piperazine of general formula (III) or a salt thereof with an urea of formula (VIII'):

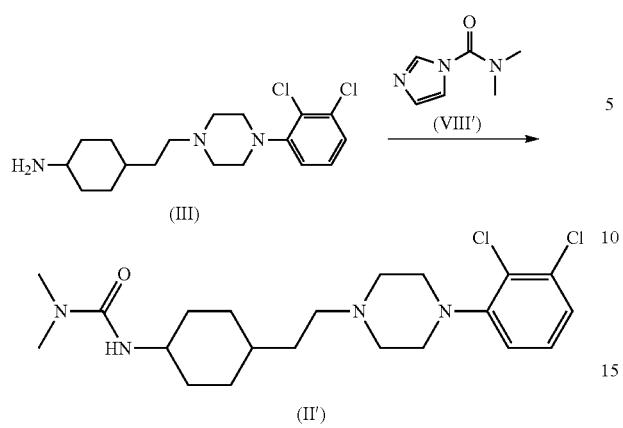

This reaction can be performed for example following the procedure described above for carrying out step a.iii.1).

The alternative scheme d.ii) can be performed when $R^2$ is imidazol-1-yl and included the following steps:

d.ii.1) treating the piperazine of general formula (III) or a salt thereof with carbonyldiimidazole (compound of formula (VIII) when $R^2$ is imidazol-1-yl):

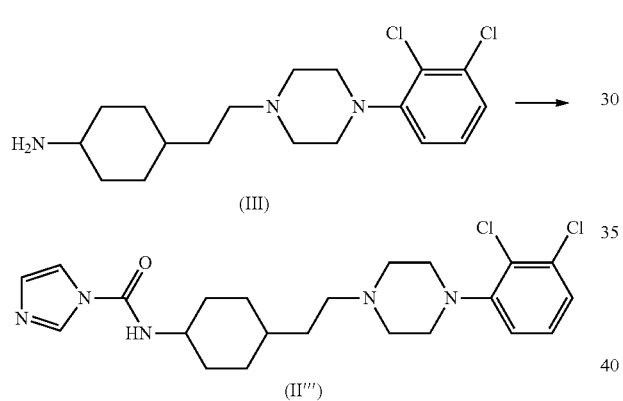

d.ii.2) treating the imidazolide of general formula (III''') with dimethylamine or a salt thereof to obtain a partial agonist of $D_2/D_3$ receptors (II').

The acylation object of step d.ii.1) can be performed for example using one of the procedures described above for carrying out step a.iii.1).

The next step d.ii.2) entails the treatment of the imidazolide of general formula (II'''), optionally isolated, with dimethylamine (or a salt thereof) to yield a partial agonist of $D_2/D_3$ receptors (II'). This step can be performed for example as described above for carrying out step a.i.2).

Said partial agonist of $D_2/D_3$ receptors (II') obtained by the processes object of the present invention can be converted into a salt (preferably the hydrochloride) or a co-crystal thereof in a further optional step.

When the piperazines of general formula (II), or any other of the compounds described in the present application, are obtained with a degree of chemical purity not suitable for the inclusion in a medicament, the processes object of the present invention entail a further step of purification, for example through chromatography or crystallization, optionally after formation of an addition compound, such as for example a salt or a co-crystal, or by washing with an organic solvent or an aqueous solution, optionally after pH adjustment.

Further aspects of the present invention are the compounds (I'), (II'''), (V) and (VI) and their stereoisomers.

The invention will be further illustrated by the following examples, in which the following abbreviations have been used:

Xantphos: 4,5-Bis(diphenylphosphino)-9,9-dimethylxantene;
TFA: trifluoroacetic acid;
CDI: 1,1'-carbonyldiimidazole;
THF: tetrahydrofuran;
Dibal-H: di-iso-butylaluminum hydride;
DMF: dimethylformamide.

Example 1

Preparation of trans-tert-butyl 4-(2-(4-(2,3-dichlorophenyl)piperazin-1-yl)ethyl)cyclohexyl carbamate

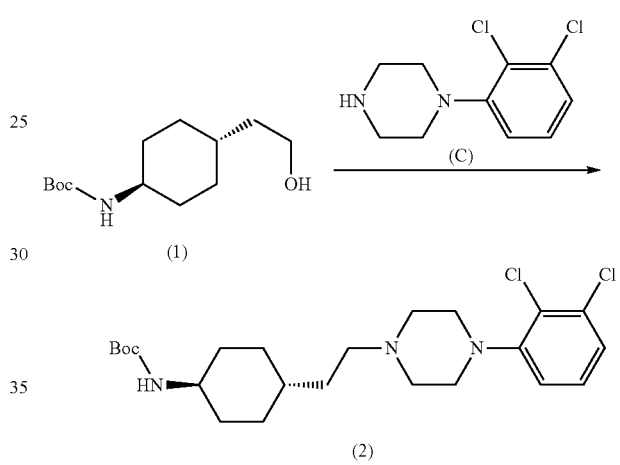

Alcohol 1 (50 mg, 0.20 mmol), 1-(2,3-dichlorophenyl)piperazine (55 mg, 0.24 mmol), $Ru_3(CO)_{12}$ (5 mg, 7.8 μmol) and Xantphos (7 mg, 12.1 μmol) are dissolved in toluene (5 mL) and the mixture is heated to the reflux temperature of the solvent for 12 hours. After solvent evaporation, the product is purified by flash chromatography eluting with $CHCl_3$/MeOH 9:1. 56 mg of compound 2 are obtained (yield: 60%).

$^1$H NMR: (400 MHz, $CDCl_3$): δ 0.98-1.05 (m, 4H), 1.19-1.21 (m, 1H), 1.36-1.40 (m, 11H), 1.72-1.75 (m, 2H), 1.94-1.96 (m, 2H), 2.36-2.40 (m, 2H), 2.58 (m, 4H), 3.02 (m, 4H), 3.33 (m, 1H), 4.36 (m, 1H), 6.90-6.93 (m, 1H), 7.06-7.11 (m, 2H).

Example 2

Preparation of trans-4-(2-(4-(2,3-dichlorophenyl)piperazin-1-yl)ethyl)cyclohexylamine

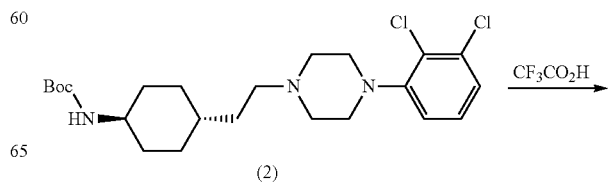

-continued

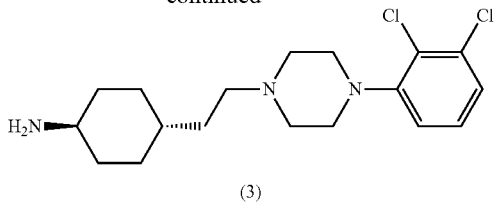

(3)

Compound 2 (300 mg, 0.66 mmol) is dissolved in a 4:1 mixture of $CH_2Cl_2$/TFA (3 mL). The mixture is allowed to react for 12 hours. After solvent evaporation, the product is purified by flash chromatography eluting with $CHCl_3$/MeOH 8:2. 205 mg of compound 3 are obtained (yield: 87%).

$^1$H NMR: (400 MHz, $CDCl_3$): δ 1.06-1.16 (m, 2H), 1.35-1.41 (m, 3H), 1.63-1.69 (m, 2H), 1.86-2.05 (m, 4H), 3.02-3.31 (m, 7H), 3.44-3.47 (m, 2H), 3.63-3.67 (m, 2H), 7.08-6.09 (m, 1H), 7.23 (m, 2H).

Example 3

Preparation of N-[trans-4-[2-[4-(2,3-dichlorophenyl)-1-piperazinyl]ethyl]cyclohexyl]-N',N'-dimethyl urea

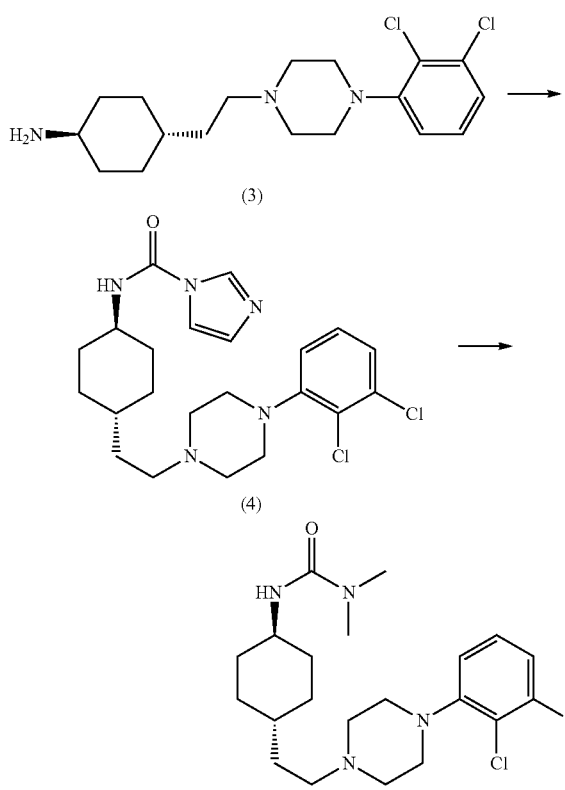

CDI (86 mg, 0.53 mmol) and compound 3 (170 mg, 0.48 mmol) are dissolved in a mixture of DMF (500 μL) and $CH_3CN$ (1.5 mL); the resulting mixture is allowed to react at room temperature for 2 hours. After solvent evaporation, the product is purified by flash chromatography eluting with $CHCl_3$/MeOH 9:1. 147 mg of compound 4 are obtained (yield: 68%).

$^1$H NMR: (400 MHz, $CDCl_3$): δ 1.02-1.43 (m, 7H), 1.77-1.81 (m, 2H), 2.02-2.05 (m, 2H), 2.41 (t, J=7.6 Hz, 2H), 2.61 (m, 4H), 3.04 (m, 4H) 3.74-3.76 (m, 1H), 6.91-5.92 (m, 1H), 6.99-7.11 (m, 3H), 7.46-7.49 (m, 1H), 7.65 (s, 1H), 8.21 (s, 1H).

$^{13}$C NMR: (100 MHz, $CDCl_3$): δ 31.4 (2C), 32.2 (2C), 33.3, 34.9, 50.3, 50.8 (2C), 52.9 (2C), 56.1, 116.1, 118.2, 121.4, 124.2, 127.0, 129.2, 134.6, 135.7, 148.1, 150.7.

Compound 4 (110 mg, 0.24 mmol) is dissolved in $CH_2Cl_2$ (3 mL); to this solution, dimethylamine hydrochloride (19 mg, 0.24 mmol) and triethylamine (52 mg, 72 μL, 151 mmol) are added. The mixture is allowed to react at room temperature for 18 hours. After solvent evaporation, the product is purified by flash chromatography eluting with $CHCl_3$/MeOH 9:1. 76 mg of Cariprazine are obtained (yield: 73%).

Example 4

Preparation of trans-3-(4-(2-hydroxyethyl)cyclohexyl)-1,1-dimethylurea

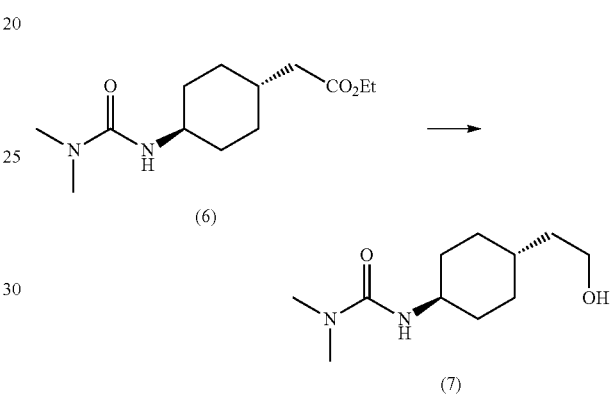

To a 0° C. cooled solution of compound 6 (500 mg, 1.95 mmol) in THF (20 mL), Dibal-H (solution 1M in THF, 5.85 mL, 5.85 mmol) is added; the mixture is allowed to react for 2 hours at 0° C. 500 μL of $H_2O$ are added and the mixture is warmed to room temperature. After about 30 minutes a colloidal precipitate forms; about 500 mg of $Na_2SO_4$ are added and after 30 minutes the mixture is filtered on a celite cake. After solvent evaporation, the product is purified by flash chromatography eluting with $CHCl_3$/MeOH 9:1, obtaining 352 mg of compound 7 (yield: 84%).

$^1$H NMR: (400 MHz, $CDCl_3$): δ 0.86-1.02 (m, 4H), 1.21-1.23 (m, 1H), 1.32 (q, J=6.8 Hz, 2H), 1.62-1.65 (m, 2H), 1.82-1.85 (m, 2H), 2.736 (s, 6H), 3.38-3.41 (m, 1H), 3.49 (q, J=6.8 Hz, 2H), 4.27 (d, J=7.2 Hz, 1H).

$^{13}$C NMR: (100 MHz, $CDCl_3$): δ 31.5 (2C), 33.0, 33.3 (2C), 35.6 (2C), 39.2, 49.4, 59.7, 157.5.

Example 5

Preparation of N-[trans-4-[2-[4-(2,3-dichlorophenyl)-1-piperazinyl]ethyl]cyclohexyl]-N',N'-dimethyl urea

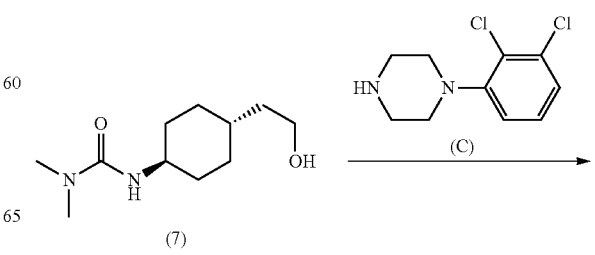

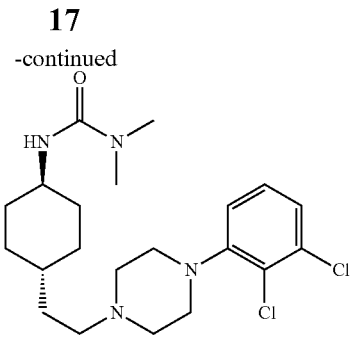

Alcohol 7 (45 mg, 0.21 mmol), 1-(2,3-dichlorophenyl)piperazine (55 mg, 0.24 mmol), Ru$_3$(CO)$_{12}$ (5 mg, 7.8 μmol) and Xantphos (7 mg, 12.1 μmol) are dissolved in toluene (5 mL) and the mixture is heated to the reflux temperature of the solvent for 12 hours. After solvent evaporation, the product is purified by flash chromatography eluting with CHCl$_3$/MeOH 9:1. 46 mg of Cariprazine are obtained (yield: 52%).

Example 6

Preparation of ethyl trans-2-(4-(dimethylcarbamoylamino)cyclohexyl)acetate

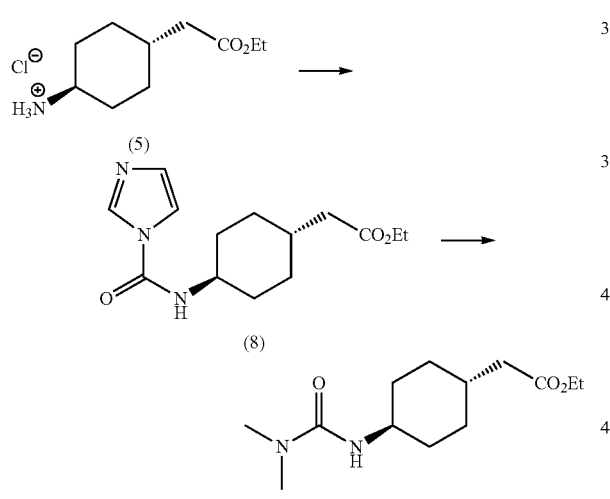

CDI (81 mg, 0.50 mmol) and compound 5 (100 mg, 0.45 mmol) are dissolved in a mixture of DMF (500 μL) and CH$_3$CN (1.5 mL); the resulting mixture is allowed to react at room temperature for 12 hours. After solvent evaporation, the product is purified by flash chromatography eluting with CHCl$_3$/MeOH 9:1. 45 mg of compound 8 are obtained (yield: 36%).

$^1$H NMR: (400 MHz, CDCl$_3$): δ 1.02-1.31 (m, 7H), 1.66-1.78 (m, 3H), 2.00-2.02 (m, 2H), 2.15 (d, J=7.2 Hz, 2H), 3.67-3.75 (m, 1H), 4.06 (q, J=7.2 Hz, 2H), 6.93 (s, 1H), 7.22 (d, J=7.6 Hz, 1H), 7.42 (s, 1H), 8.12 (s, 1H).

$^{13}$C NMR: (100 MHz, CDCl$_3$): δ 13.8, 31.0 (2C), 31.9 (2C), 33.4, 40.9, 49.8, 60.0, 116.1, 129.1, 135.5, 147.9, 172.6.

Compound 8 (45 mg, 0.16 mmol) is dissolved in CH$_2$Cl$_2$ (2 mL); to this solution, dimethylamine hydrochloride (13 mg, 0.16 mmol) and triethylamine (34 mg, 47 μL, 0.34 mmol) are added. The mixture is allowed to react at room temperature for 18 hours. After solvent evaporation, the product is purified by flash chromatography eluting with CHCl$_3$/MeOH 9:1. 32 mg of compound 6 are obtained (yield: 78%).

$^1$H NMR: (400 MHz, CDCl$_3$): δ 1.01-1.07 (m, 4H), 1.13 (t, J=7.2 Hz, 3H), 1.62-1.67 (m, 3H), 1.87-1.89 (m, 2H), 2.06 (d, J=6.4 Hz, 2H), 2.76 (s, 6H), 3.43-3.47 (m, 1H), 3.39 (q, J=7.2 Hz, 2H), 4.21 (d, J=7.2 Hz, 1H).

$^{13}$C NMR: (100 MHz, CDCl$_3$): δ 13.7, 31.2 (2C), 33.1 (2C), 33.7, 35.6 (2C), 41.0, 49.0, 59.6, 157.3, 172.4.

Example 7

Preparation of N-[trans-4-[2-[4-(2,3-dichlorophenyl)-1-piperazinyl]ethyl]cyclohexyl]-N',N'-dimethyl urea

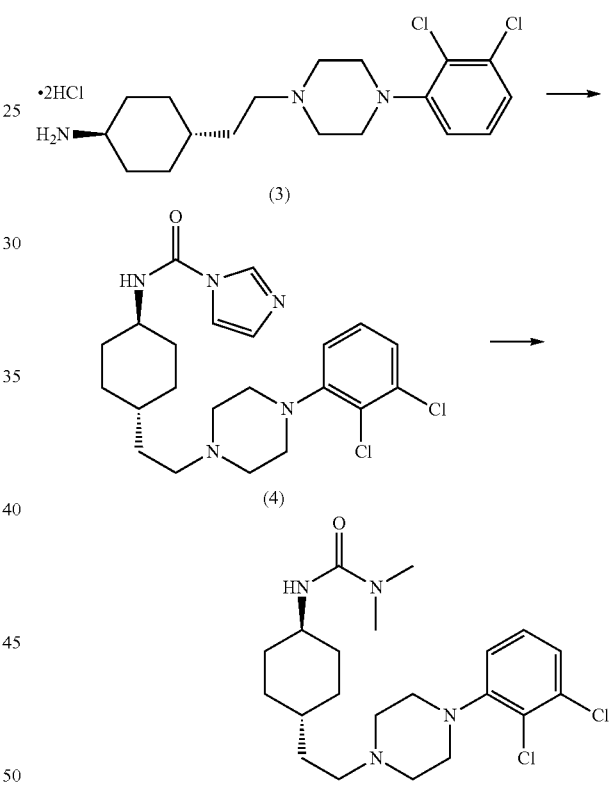

The dihydrochloride salt of compound 3 (17.0 g, 39.6 mmol) is suspended at room temperature in CH$_2$Cl$_2$ (150 mL), then triethylamine (13.6 g, 134.6 mmol) and CD, (7.7 g, 47.5 mmol) are slowly added. The mixture is maintained under stirring for 30 minutes (until complete CO$_2$ evolution) at room temperature, then dimethylamine hydrochloride (4.2 g, 51.5 mmol) is added, and the mixture is allowed to react at room temperature for 36 hours.

When the reaction is complete, the mixture is cooled to 0-5° C. and stirred for 2 hours, then it is filtered and the solid obtained is washed with water. The product is dried at 45° C. under reduced pressure yielding 14.0 g of the desired compound (yield: 83%).

The solid obtained can be further crystallized by methanol, iso-propanol, acetonitrile or ethyl acetate.

The invention claimed is:

1. N-[4-[2-[4-(2,3-dichlorophenyl)piperazin-1-yl]ethyl]cyclohexyl]-imidazol-1-carboxamide (II'''):

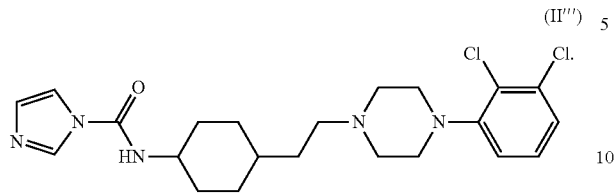

2. A process for preparing Cariprazine or a salt thereof comprising treating N-[4-[2-[4-(2,3-dichlorophenyl)piperazin-1-yl]ethyl]cyclohexyl]imidazol-1-carboxamide (II'''):

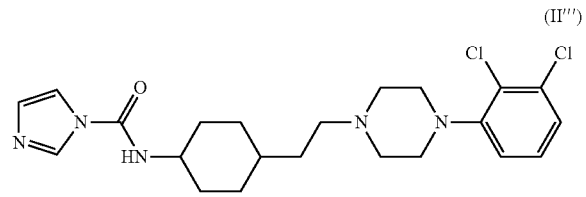 [SMILES: O=C(NC1CCC(CCN2CCN(c3cccc(Cl)c3Cl)CC2)CC1)n1ccnc1]

with dimethyl amine or a salt thereof.

3. A process according to claim 2, wherein N-[4-[2-[4-(2,3-dichlorophenyl)piperazin-1-yl]ethyl]cyclohexyl]imidazol-1-carboxamide (II''') is prepared according to the following synthetic steps:

a) providing an alcohol of formula (I''):

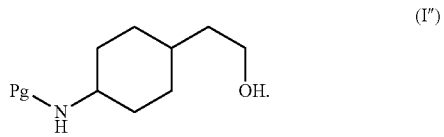

wherein Pg is a protecting group of amines;

b) directly alkylating 1-(2,3-dichlorophenyl)piperazine (C):

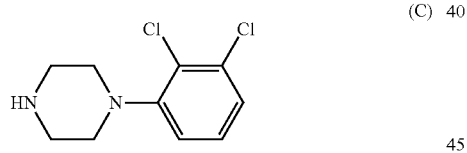

with the alcohol of formula (I'') to yield a piperazine of formula (II''):

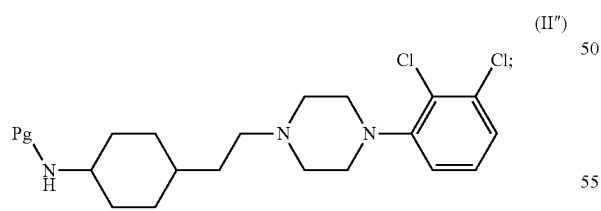

c) deprotecting the compound of formula (II'') to yield a piperazine of formula (III):

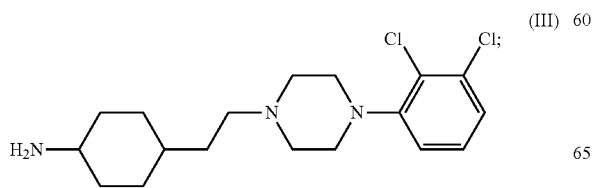

d) treating the piperazine of formula (III) or a salt thereof with a compound of formula (VIII):

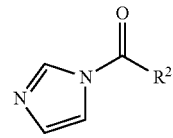

wherein $R^2$ is selected from imidazol-1-yl and —N$(CH_3)_2$.

4. The process according to claim 3, wherein step b) is carried out in the presence of a catalyst comprising a transition metal, in an apolar solvent or in a protic or aprotic polar solvent.

5. The process according to claim 4, wherein the transition metal is selected from the group consisting of rhodium, nickel, palladium, platinum, iridium, ruthenium or a mixture thereof and is used in metallic form or in the form of a salt or a coordination complex thereof.

6. The process according to claim 5, wherein step b) is carried out under homogenous catalysis conditions and the transition metal is used in the form of a coordination complex soluble in the reaction medium.

7. The process according to claim 4, wherein step b) is carried out under homogenous catalysis conditions and the transition metal is used in the form of a coordination complex soluble in the reaction medium.

8. The process according to claim 3, wherein the alcohol used as reagent in the alkylation reaction of 1-(2,3-dichlorophenyl)piperazine in step b) is a trans-2-(4-aminocyclohexyl)ethanol of formula (IA):

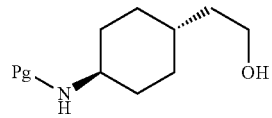

and said alkylation reaction leads to the formation of a piperazine of formula (IIA) in which the substituents attached to cyclohexane ring possess 1,4-trans relative configuration:

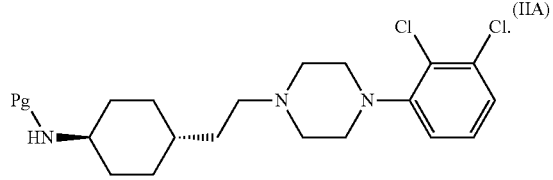

9. 3-[4-(2-hydroxyethyl)cyclohexyl]-1,1-dimethylurea (I'):

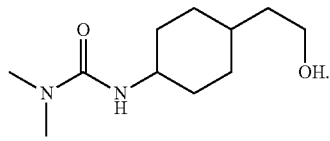

* * * * *